United States Patent [19]

Kobayashi et al.

[11] Patent Number: 4,648,812
[45] Date of Patent: Mar. 10, 1987

[54] METHOD AND APPARATUS FOR PREVENTING PULSATIONS

[75] Inventors: Susumu Kobayashi, Fujinomiya; Hideyuki Morikawa, Tokyo, both of Japan

[73] Assignee: Terumo Corporation, Tokyo, Japan

[21] Appl. No.: 763,077

[22] Filed: Aug. 5, 1985

Related U.S. Application Data

[63] Continuation of Ser. No. 597,220, Apr. 5, 1984, abandoned, which is a continuation of Ser. No. 491,786, May 9, 1983, abandoned, which is a continuation of Ser. No. 231,952, Feb. 6, 1981, abandoned.

[30] Foreign Application Priority Data

Feb. 12, 1980 [JP] Japan ................................. 55-15645

[51] Int. Cl.$^4$ ............................................. F04B 43/08
[52] U.S. Cl. .................................................. 417/477
[58] Field of Search ............... 417/474, 477, 478, 479, 417/475

[56] References Cited

U.S. PATENT DOCUMENTS

| | | | |
|---|---|---|---|
| 2,412,397 | 12/1946 | Harper | 417/474 |
| 2,877,714 | 3/1959 | Sorg et al. | 417/474 |
| 3,083,647 | 4/1963 | Muller | 417/474 |
| 3,726,613 | 3/1973 | Von Casimir | 417/477 |
| 3,791,400 | 2/1974 | Hrdina | 417/477 |
| 3,826,593 | 7/1974 | Von Casimir | 417/477 |
| 4,210,138 | 7/1980 | Jess | 417/477 |
| 4,213,454 | 7/1980 | Shim . | |

FOREIGN PATENT DOCUMENTS

| | | | |
|---|---|---|---|
| 2543300 | 2/1977 | Fed. Rep. of Germany | 417/474 |
| 54-90891 | 7/1979 | Japan . | |
| 8001934 | 9/1980 | World Int. Prop. O. . | |
| 1081818 | 9/1967 | United Kingdom | 417/474 |
| 923443 | 4/1973 | United Kingdom | 417/474 |

Primary Examiner—Carlton R. Croyle
Assistant Examiner—Timothy S. Thorpe
Attorney, Agent, or Firm—Frishauf, Holtz, Goodman & Woodward

[57] ABSTRACT

Pulsations of a peristaltic type fluid-infusion pump are prevented by providing pulsations of opposite phase to that of the pulsations occurring during fluid infusion by the peristaltic type fluid-infusion pump.

16 Claims, 11 Drawing Figures

METHOD AND APPARATUS FOR PREVENTING PULSATIONS

This application is a continuation of application Ser. No. 597,220, filed Apr. 5, 1984, which in turn is a continuation of Ser. No. 491,786, filed May 9, 1983, which in turn is a continuation of Ser. No. 231,952, filed Feb. 6, 1981, all now abandoned.

BACKGROUND OF THE INVENTION

The present invention relates to a method and apparatus for preventing pulsations in a peristaltic fluid-infusion pump for fluid infusions.

A peristaltic type pump, for example, a peristaltic type fluid-infusion finger pump is constructed to deliver fluid inside an elastic tube by closing the tube under pressure and displacing the points of closure sequentially. When the points of closure reach the outlet port, they return to the inlet port in a peristaltic type fluid-infusion finger pump. When the points of closure return to the inlet port, the closure under pressure at the outlet port is released. Due to the relative positions of the inlet and outlet ports, the fluid inside the tube is spontaneously displaced independently of the operation of the pump. Thus, a general peristaltic type fluid-infusion finger pump is so constructed that at least one point of closure is present at all times. Although the fluid infusion is continuously performed while the points of closure are sequentially displaced as described above, the fluid delivery is interrupted when the closure under pressure is released at the outlet port. Furthermore, with a fluid-infusion finger pump, the pressure plate is slightly vibrated in the front-back direction, and fine pulsations are caused when the point of closure changes from one finger to the other. It is preferable that the fluid be continuously delivered at a constant flow rate in fluid infusions. Thus, a peristaltic type fluid-infusion pump which does not cause pulsations has been desired.

SUMMARY OF THE INVENTION

It is, therefore, the primary object of the present invention to provide a method and apparatus for preventing pulsations in a peristaltic type fluid-infusion pump.

There is provided according to the present invention a method for preventing pulsations in a peristaltic type fluid-infusion pump wherein pulsations opposite to fluid pulsations occurring during fluid infusion by a peristaltic type fluid-infusion pump are supplied to the fluid.

According to another aspect of the present invention, there is also provided an apparatus for preventing fluid pulsations in a peristaltic type fluid-infusion pump comprising means mounted at the portion of the peristaltic type fluid-infusion pump, which corresponds to the portion of the pump tube that the fluid pulsations occur, for providing pulsations which are opposite to the fluid pulsations.

DETAILED DESCRIPTION OF THE INVENTION

Figure 1:
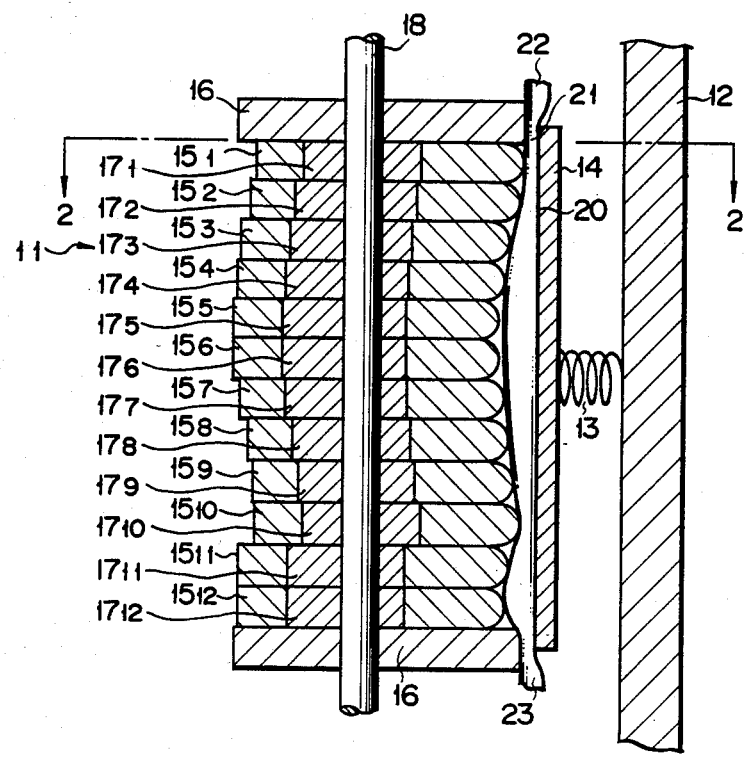
FIG. 1 is a sectional view of a peristaltic type fluid-infusion finger pump having an apparatus for preventing pulsations according to one embodiment of the present invention.
Figure 2:
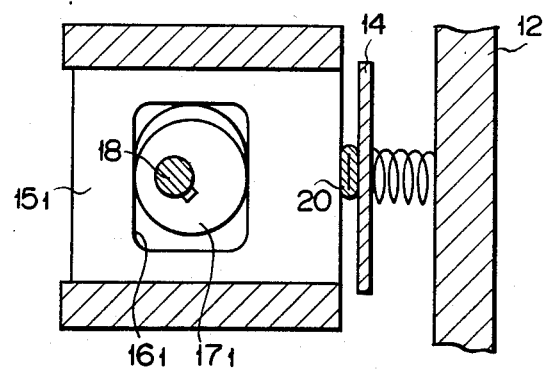
FIG. 2 is a sectional view along the line 2—2 of the peristaltic type fluid-infusion finger pump of FIG. 1.
Figure 3:
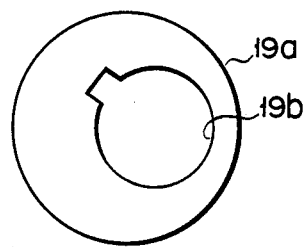
FIG. 3 is a plan view of a fluid infusion cam.
Figure 4:
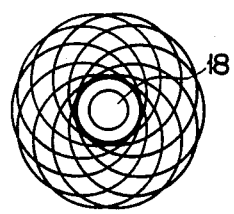
FIG. 4 is a perspective plan view from the top of a plurality of superposed fluid-infusion eccentric cams.
Figure 5:
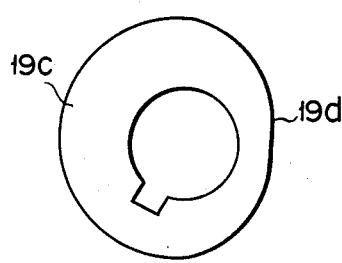
FIG. 5 is a plan view of a pulsation-correction cam.
Figure 6:
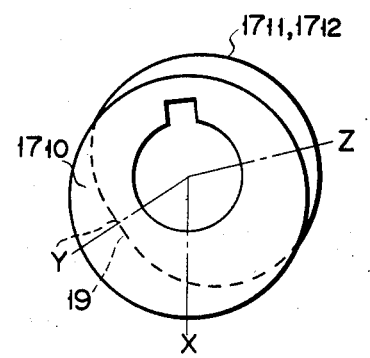
FIG. 6 is a plan view of the fluid-infusion eccentric cam and pulsation-correction cams superposed.

In a finger pump 11 as shown in FIG. 1, a pressure plate 14 is supported by a spring 13. In opposition to this pressure plate 14 are arranged fluid-infusion finger members $15_1$ to $15_{10}$ and pulsation-correction finger members $15_{11}$ and $15_{12}$. Rectangular cam holes $16_1$ to $16_{12}$ are formed in the finger members $15_1$ to $15_{12}$, respectively, as shown in FIG. 2. Eccentric fluid-infusion cams $17_1$ to $17_{12}$ are housed in these cam holes $16_1$ to $16_{12}$ respectively. Each of the eccentric cams $17_1$ to $17_{10}$ has, as shown in FIG. 3, a circular cam surface $19a$ and an eccentric shaft hole $19b$. These eccentric cams $17_1$ to $17_{10}$ are mounted on a shaft 18 and shifted through a predetermined angle, for example, 36 degrees from one another as shown in FIG. 4. The cams $17_1$ to $17_{10}$, mounted on shaft 18, form a stacked cam block. On this shaft 18 are also mounted pulsation-correction eccentric cams $17_{11}$ and $17_{12}$ housed in the cam holes $16_{11}$ and $16_{12}$ of the pulsation-correction finger members $15_{11}$ and $15_{12}$, respectively. The eccentric cams $17_{11}$ and $17_{12}$ have an arc cam surface $19c$ and a flat cam surface $19d$ as shown in FIG. 5. The strokes of these eccentric cams $17_{11}$ and $17_{12}$ are set to be shorter than those of the eccentric cams $17_1$ to $17_{10}$. The flat cam surface $19d$ is arranged at the side of the shortest stroke. FIG. 6 shows the relation of the fluid-infusion eccentric cam $17_{10}$ with the correction eccentric cams $17_{11}$ and $17_{12}$. Referring to FIG. 6, when the point of the maximum stroke, that is, the top dead center of the eccentric cam $17_{10}$ is defined as X, the point of the shortest stroke, that is, the bottom dead center of the eccentric cams $17_{11}$ and $17_{12}$ is defined as Y, the point of the maximum stroke, that is, the top dead center of the cams $17_{11}$ and $17_{12}$ is defined as Z, and the central position of the shaft is defined as O, then the cams $17_{10}$, $17_{11}$ and $17_{12}$ are so arranged that XOY is 55° and XOZ is 105.4°.

Figure 7:
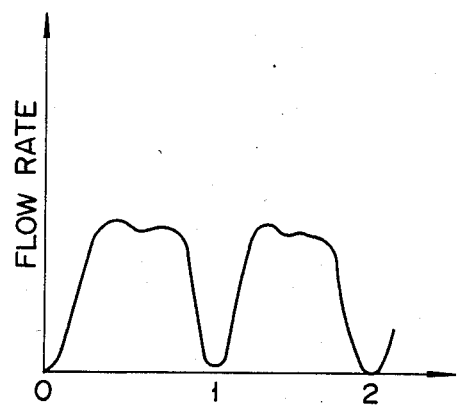
FIG. 7 is a view of the waveform of the fluid delivery by the fluid-infusion fingers.
Figure 8:
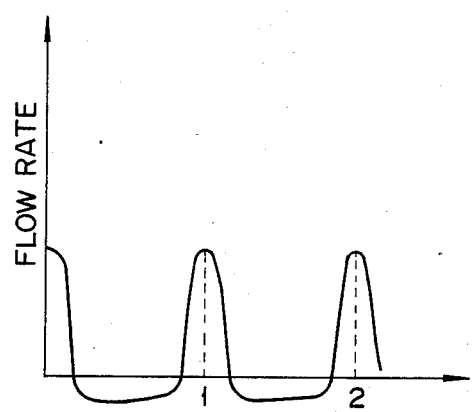
FIG. 8 is a view of the waveform of the pulsation obtained by the pulsation-correction fingers.

A tube 20 of soft vinyl chloride of 2.5 mm inner diameter and 4.0 mm outer diameter is clamped between the finger members $15_1$ to $15_{12}$ and the pressure plate 14. The pressure plate 14 presses the tube 20 toward the finger members $15_1$ to $15_{12}$ by the biasing force of the spring 13 so that the tube 20 is closed under pressure at all times by any of the fluid-infusion finger members $15_1$ to $15_{12}$. When the cam shaft 18 rotates together with the cams $17_1$ to $17_{12}$ under this condition, the finger members $15_1$ to $15_{12}$ start moving to perform peristaltic action on the tube 20. Thus, the fluid-infusion fingers $15_1$ to $15_{10}$ sequentially displace points of closure 21 of the tube 20. The fluid inside the tube is fed from an inlet section or inlet port 22 to an outlet section or outlet port 23 in this manner. When the fluid is fed by the fluid-infusion finger members $15_1$ to $15_{10}$, the flow rate of the fluid inside the tube 20 changes as shown in FIG. 7, that is, pulsations occur on the outlet side of the tube 20. When a pulsation waveform of the opposite phase to this pulsation waveform (FIG. 8) is formed, the two pulsation waveforms cancel each other so that a constant fluid-transfusion waveform may be obtained. According to the present invention, the pulsation of the opposite waveform is generated by the pulsation-correction cams $17_{11}$ and $17_{12}$. When the flow rate becomes small with the waveform (FIG. 7) of the fluid fed by the fluid-infusion finger members $15_1$ to $15_{10}$, the pulsation-correction finger members $15_{11}$ and $15_{12}$ press the tube 20 to increase the flow rate at the outlet port 23 by the volume of the crushed tube. In this case, at the top dead center Z of the correction cams $17_{11}$ and $17_{12}$, pulsation-correction finger members $15_{11}$ and $15_{12}$ are pressed. When the flow rate is great with the fluid waveform, the pulsation-correction finger members $15_{11}$ and $15_{12}$ are gradually withdrawn from the tube 20. The pulsation-correction cams $17_{11}$ and $17_{12}$ rotate so that the top dead center Z is replaced by the bottom dead center Y. As the pulsation-correction finger members $15_{11}$ and $15_{12}$ are withdrawn, the tube 20 recovers its original shape by its elasticity, and the volume of the fluid fed at the outlet port 23 is reduced by the volume of the crushed tube. The rate of the volume of fluid fed from the outlet port 23 becomes constant by performing compression and expansion of the tube 20 at the outlet port 23 according to the waveform of the fed fluid.

Figure 9:
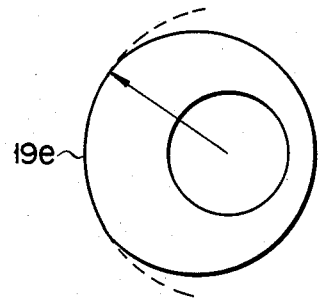
FIG. 9 is a view illustrating a modification of the fluid-infusion eccentric cams.

When the shaft 18 rotates under the condition that the finger member $15_1$ closes the tube 20 under pressure in cooperation with the pressure plate 14 at the extreme end of the inlet port 22 in the peristaltic type finger pump as described above, the finger member $15_1$ is withdrawn and the finger member $15_2$ presses the tube 20 instead. Since the thickness of the tube 20 is constant, the pressure plate 14 moves forward as the first finger member $15_1$ withdraws. When the finger member $15_2$ advances, the pressure plate 14 is returned by the finger member $15_2$. When the shaft 18 rotates further, the finger member $15_3$ replaces the finger member $15_2$ so that the finger member $15_3$ instead of the finger $15_2$ closes the tube 20 by pressure. The pressure plate 14 moves in the front-back direction with each replacement among the fluid-infusion finger members $15_1$ to $15_{10}$. Since it is difficult due to various conditions of the design of the cams to eliminate such front-back movement of the pressure plate by the pulsation-correction fingers $15_{11}$ and $15_{12}$ which are driven by the pulsation-correction cams $17_{11}$ and $17_{12}$, it is preferable that the pressure plate never undergo this front-back movement. For this purpose, the fluid-infusion finger cams $17_1$ to $17_{10}$ form an arc-shaped surface $19e$ corresponding to the arc around the eccentric shaft, as shown in FIG. 9. When cams having such an arc-shaped surface $19e$ are used, the cams $17_1$ to $17_{10}$, mounted on the shaft 18 and shifted from each other through 36°, form at their peripheries a substantially complete circle. Each of the cams $17_1$ to $17_{10}$ has a section having a curvature equal to that of a circle formed with a rotation axis of the cam shaft as a center and enclosing the stacked cams $17_1$ to $17_{10}$. Due to this, when the fluid-infusion eccentric cams $17_1$ to $17_{10}$ rotate, the finger members $15_1$ to $15_{10}$ will not move to displace the pressure plate 14 in the front-back direction.

The method for producing the shapes of the pulsation-correction cams $17_{11}$ and $17_{12}$ will now be described.

Figure 10:
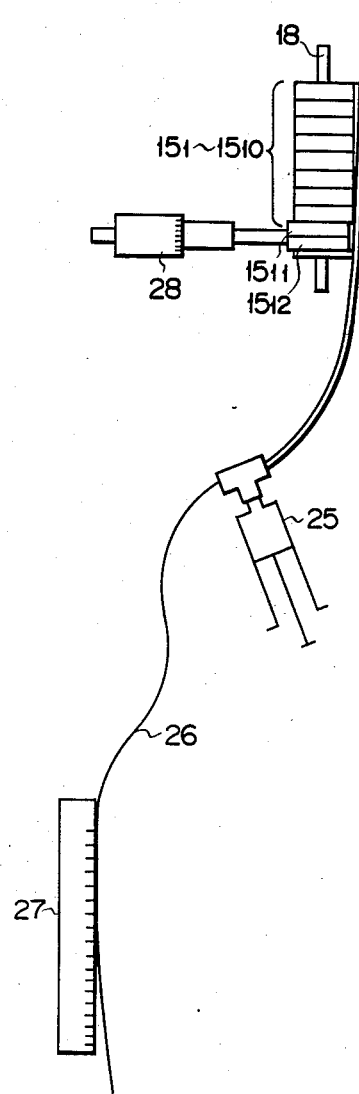
FIG. 10 is a view for explaining the measuring method for designing the pulsation-correction cams.

FIG. 10 shows a method which is based on actual measurements. According to this method, the fluid is first fed in an amount corresponding to one revolution of the shaft 18 of the finger pump. During such time, the fluid is fed to an ultrafine tube 26 through a cylinder 25. The fluid fed to the ultrafine tube 26 is measured in units of length, and this length l is divided into segments, for example, n(100) segments. This length l/n is defined as $\alpha$. The shaft 18 is set to angle 0, and the fluid level inside the ultrafine tube 26 is set to 0 of a scale 27. Under this condition, the shaft 18 is rotated through $360°/n(100)$, and the pulsation-correction finger members $15_{11}$ and $15_{12}$ are displaced in the front-back direction by adjusting a micrometer 28 so that the fluid level of the ultrafine tube 26 comes to the position of the length $\alpha$ of the scale 27. The indicated value of the micrometer 28 is read when the fluid level of the ultrafine tube 26 is aligned with the reading of $\alpha$ of the scale 27. The piston of the cylinder 25 is moved next, the fluid level of the ultrafine tube 26 is aligned with the value 0 of the scale 27, and the shaft 18 is rotated through $360°/n(100)$ again. These procedures are repeated until the shaft completes one revolution. The movements of the pulsation-correction finger members are obtained from the micrometer measurements when the shaft completes one revolution. The pulsation-correction finger members are designed based on these measurements.

The method for obtaining the shapes of the correction cams by calculation will be described next. When the tube is crushed in the direction perpendicular to its axis, the cross section of the tube being crushed is first an ellipse, then an extremely elongated circle, and finally comes to resemble eyeglass frames just before the tube is completely crushed. The changes in the shape are different depending upon the material of the tube, the ratio of the wall thickness of the tube to the diameter thereof, and the like. However, the basic tendency seems to be the same. In the case of a peristaltic type fluid-infusion finger pump, the flow rate is determined by changes in the volume within the tube which is in turn determined by changes in the shape of the tube. The change in the volume of the tube is greatest when the cross section of the tube is changing from an ellipse to elongated circle. Accordingly, it is assumed that the volume of the tube changes approximately with the elongated circular cross-sectional area of the tube.

Figure 11:
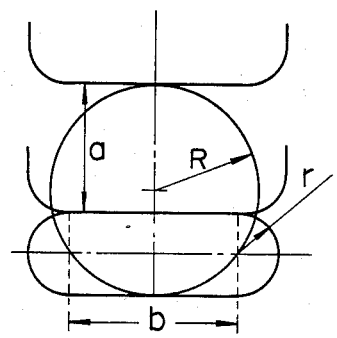
FIG. 11 is a view illustrating the state in which the tube is pressed by the fingers.

FIG. 11 shows the circular cross section of the tube before it is crushed by the finger members, superposed on the elongated circular cross section of the tube when it is slightly smashed. The cross-sectional area of the tube before crushing is $S_0$, $$S_0 = \pi R^2 \tag{1}$$

From FIG. 11, $$2R = a + 2r \tag{2}$$

$$2\pi R = 2\pi r + 2b \tag{3}$$

where a is the diameter reduction of the tube crushed by the finger members, and b is the length of the horizontal part of the elongated circle.

The cross-sectional area of the tube after crushing is S, $$S = \pi r^2 + 2br \quad (4)$$

When equations (2) and (3) are substituted into equation (4), this gives $$r = \frac{2R - a}{2} \quad (2')$$

$$b = \frac{1}{2}\pi a \quad (3')$$

$$S = \pi \left(\frac{2R - a}{2}\right)^2 + \pi a \left(\frac{2R - a}{2}\right) \quad (5)$$

$$= \pi R^2 - \pi \left(\frac{a}{2}\right)^2 \quad (5')$$

where a is determined by the angle of the eccentric cam and the eccentricity. When the stroke of the finger member in the front-back direction (i.e., the direction in which the finger member moves from its rearmost position to its frontmost position; horizontally in FIG. 1) is 2R, and the tube is assumed to return to its circular shape as the finger member is most withdrawn, the eccentricity of the eccentric cam is R. If the finger member is most withdrawn (i.e., rearmost position) when the angle of rotation of the eccentric cam is 0° (i.e., the cam is in its "start" position where the finger member is in its rearmost position), $$a = R - R\cos\theta \quad (6)$$

where, θ is the angle of the eccentric cam. When equation (6) is substituted into equation (5'), $$S = \pi R^2 - \pi \left(\frac{R - R\cos\theta^2}{2}\right) \quad (7)$$

The volume change v of the tube crushed by the finger member is obtained by multiplying the thickness t of the finger member by this value, provided that the cross-sectional area of the tube does not change along the axis of the tube. Thus, $$V = t\left\{\pi R^2 - \pi \left(\frac{R - R\cos\theta^2}{2}\right)\right\} \quad (8)$$

The flow rate is obtained by the change in the volume of the tube at the outlet port of the pump. When this finger at the point of closure is the nth finger, the volume of the tube crushed by the finger member is $$V = \sum_{K=n}^{10} t\left\{\pi R^2 - \pi \left(\frac{R - R\cos\theta \, K^2}{2}\right)\right\} \quad (9)$$

where θ is 36° assuming the number of finger members is 10. If the value of V is obtained by varying n from 1 through 10, or further dividing 36° for a smaller angle, the volume of the tube for this angle is obtained. The flow rate per angle can thus be obtained by obtaining the difference in the values of V. Although the flow rate thus obtained has pulsation, the movements of the pulsation-correction cams and the finger members are calculated to produce the opposite pulsation.

By using the pulsation-correction cams designed by the measurements or calculations described above, pulsation in the peristaltic type fluid-infusion finger pump is prevented so that constant flow ideal for the fluid-infusion pump may be obtained. This allows injection of antihypertensive drug, fluid-infusion with a small but constant flow rate for an infant, or the like so that ill effects of irregular flow rate may be eliminated. Since the pulsation-correction cams may also be mounted on the shaft of the fluid-infusion finger members of the finger pump, the number of required parts may be decreased.

Although the present invention has been described as applied to a peristaltic type fluid-infusion finger pump, it is to be understood that the present invention is also applicable to a peristaltic type fluid-infusion roller pump. The peristaltic fluid-infusion pump is used for transfusion of blood as well as medical fluid. In the embodiments, the pulsation preventing apparatus is disposed on the peristaltic type pump but this may be independently provided.

What we claim is:

1. A peristaltic fluid-infusion finger pump apparatus comprising:

a peristaltic fluid-infusion finger pump which includes a plurality of fluid-infusion finger members arranged in an array of first to last stage fluid-infusion members each having a respective cam hole, cam means including a rotatable cam shaft and a plurality of eccentric cams mounted on said cam shaft for rotation with said cam shaft and stacked on said cam shaft to form a stacked cam block, said cam shaft being rotatable about a longitudinal rotation axis thereof, said eccentric cams being arranged as first to last stage eccentric cams respectively received in said cam holes of said fluid-infusion finger members, said eccentric cams being shifted from each other on said cam shaft through a predetermined angle;

each of said eccentric cams driving a respective fluid-infusion member through a given stroke, each of said eccentric cams having at a maximum stroke section thereof an arc-shaped cam surface portion having a curvature the radius of which is equal to that of a right circle formed with a rotation axis of said cam shaft as a center, and an outer circular contour line formed by the curvature of the stacked cam block being equal to the right circle at an upper end view;

a pressure plate facing said array of said first to last stage fluid-infusion finger members with an elastic tube clamped therebetween;

driving means coupled to said cam shaft to rotate said cam shaft together with said eccentric cams, whereby said fluid-infusion finger members are successively moved through a given stroke to apply a peristaltic movement to said elastic tube when said eccentric cams are rotated together with said cam shaft to infuse fluid through said elastic tube, said infused fluid having small fluid-infusion pulsations; and pulsation correction means disposed at an outlet side of said peristaltic fluid-infusion finger pump, said pulsation correction means including:

at least one pulsation correction finger member having a cam hole therein; and at least one further eccentric cam received in said cam hole of said at least one pulsation correction finger member, said at least one further eccentric cam being mounted on said cam shaft and being rotatably driven by said cam shaft;

said at least one pulsation correction finger member being moved by said at least one further eccentric cam and being coupled to said elastic tube for applying a pulsation waveform opposite to the waveform of fluid-infusion pulsations occurring on the outlet side of said peristaltic pump to said elastic tube to substantially cancel out said fluid-infusion pulsations.

2. The peristaltic fluid-infusion finger pump apparatus of claim 1, wherein said circle formed with a rotation axis of said cam shaft as a center extends substantially perpendicular to said rotation axis of said cam shaft.

3. The peristaltic fluid-infusion finger pump apparatus of claim 2, wherein said stacked cam block, at said upper end view thereof, forms a right-cylindrical contour line.

4. The peristaltic fluid-infusion finger pump apparatus of claim 1, wherein said stacked cam block, at said upper end view thereof, forms a right-cylindrical contour line.

5. The peristaltic fluid-infusion finger pump apparatus of claim 1, wherein said peristaltic fluid-infusion finger pump comprises ten of said fluid-infusion finger members and ten of said first mentioned eccentric cams.

6. The peristaltic fluid-infusion finger pump apparatus of claim 1, wherein said eccentric cams of said peristaltic fluid-infusion finger pump are arranged on said cam shaft so as to be shifted through 36° from each other.

7. The peristaltic fluid-infusion finger pump apparatus of claim 1, wherein said at least one pulsation correction finger member is arranged adjacent the last stage fluid-infusion finger member.

8. The peristaltic fluid-infusion finger pump apparatus of claim 1, comprising at least two of said pulsation correction finger members and at least two further eccentric cams received in said cam holes of respective pulsation correction finger members, said at least two pulsation correction finger members being arranged adjacent said last stage fluid-infusion finger member of said peristaltic fluid-infusion finger pump.

9. The peristaltic fluid-infusion finger pump apparatus of claim 1, wherein said pressure plate additionally faces said at least one pulsation correction finger member, said elastic tube having a portion clamped between said pressure plate and said at least one pulsation correction finger member.

10. The peristaltic fluid-infusion finger pump apparatus of claim 9, wherein all of said first to last stage fluid-infusion finger members and said at least one pulsation correction finger member are arranged immediately adjacent each other in a row.

11. The peristaltic fluid-infusion finger pump apparatus of claim 1, wherein said at least one further eccentric cam has an arc-shaped surface portion and a flat-shaped surface portion, the stroke of said at least one further eccentric cam being shorter than those of said eccentric cams of said peristaltic fluid-infusion finger pump.

12. The peristaltic fluid-infusion finger pump apparatus of claim 5, wherein said eccentric cams of said peristaltic fluid-infusion finger pump are arranged on said cam shaft so as to be shifted through 36° from each other.

13. The peristaltic fluid-infusion finger pump apparatus of claim 5, wherein said at least one pulsation correction finger member is arranged adjacent the last stage fluid-infusion finger member.

14. The peristaltic fluid-infusion finger pump apparatus of claim 8, wherein said pressure plate additionally faces said at least one pulstation correction finger member, said elastic tube having a portion clamped between said pressure plate and said at least one pulsation correction finger member.

15. The peristaltic fluid-infusion finger pump apparatus of claim 14, wherein all of said first to last stage fluid-infusion finger members and said at least one pulsation correction finger member are arranged immediately adjacent each other in a row.

16. The peristaltic fluid-infusion finger pump apparatus of claim 8, wherein said at least one further eccentric cam has a arc-shaped surface portion and a flat-shaped surface portion, the stroke of said at least one further eccentric cam being shorter than those of said eccentric cams of said peristaltic fluid-infusion finger pump.

* * * * *